United States Patent [19]
Fibi et al.

[11] Patent Number: 5,457,089
[45] Date of Patent: Oct. 10, 1995

[54] MUTEINS OF HUMAN ERYTHROPOIETIN, THE PREPARATION THEREOF AND THE USE THEREOF

[75] Inventors: Mathias Fibi, Marburg; Gerd Zettlmeissl, Lahntal; Hans Küpper, Marburg, all of Germany

[73] Assignee: Behringwerke Aktiengesellschaft, Marburg, Germany

[21] Appl. No.: 272,375

[22] Filed: Jul. 6, 1994

Related U.S. Application Data

[63] Continuation of Ser. No. 152,919, Nov. 16, 1993, abandoned, which is a continuation of Ser. No. 799,898, Dec. 2, 1991, abandoned, which is a division of Ser. No. 553,593, Jul. 18, 1990, abandoned.

[30] Foreign Application Priority Data

Jul. 20, 1989 [DE] Germany .................. 39 23 963.2

[51] Int. Cl.$^6$ .................. A61K 38/18; A61K 38/19; A61K 38/22; A61K 38/17
[52] U.S. Cl. .................. 514/8; 514/12; 424/85.1; 435/69.4
[58] Field of Search .................. 435/69.4; 530/399, 530/397; 514/12, 8, 21; 424/85.1

[56] References Cited

U.S. PATENT DOCUMENTS 4,703,008  10/1987  Lin .................. 435/240.2
4,835,260   5/1989  Shoemaker .................. 530/397

OTHER PUBLICATIONS

Rolson et al. 1986. *Introduction to Protein and Protein Engineering*, Elsevier, New York, N.Y. p. 41.
Jacobs et al., Nature, 313:806–809 (1985).
Dordal et al., Endocrinology, 116:2293–2299 (1985).
Letsinger et al., J. Amer. Chem Soc., 97:3278–3279 (1975).
Letsinger et al., J. Amer. Chem Soc., 98:3655–3661 (1976).
Morinaga et al., Bio/Technology, 7:636–639 (1984).
Kramer et al., Nucl. Acids. Res. 12:9441–9456.
Sanger et al., Proc. Natl. Acad. Sci., USA 74:5463–5467 (1977).
Zettlmeissl et al., Behring Inst. Mitt., 82:26–34 (1988).
Graham et al., Virology, 52:456–467 (1973).
Lee et al., Nature (London), 294:228–232 (1981).
Hudziak et al., Cell, 31:137–146 (1982).
Hales et al., Biochem., J., 88:137–146 (1983).
Tejedor et al., Analyt. Biochem., 127:143–149 (1982).
Smith et al., Analyt. Biochem., 150:76–85 (1985).
Krystal, J. Exp. Hematol., 11:649–660 (1983).
Recny et al., J. Biol. Chem., 262:17156–63 (1987).
Bowie et al. 1990. Science 247:1306–1310.
Dayhoff et al. 1972. *Atlas of Protein Sequence and Structure* vol. 5 89–99.
Shoemaker et al. 1986. Molecular and Cellular Biology 6(3): 849–858.
Dubé et al. 1988. J. Biol. Chem. 263(33): 17516–17521.
Rege et al. 1982. J. Lab Clin Med., 100(6): 829–843.

*Primary Examiner*—Keith C. Furman
*Attorney, Agent, or Firm*—Finnegan, Henderson, Farabow, Garrett & Dunner

[57] ABSTRACT

The invention relates to muteins of human erythropoietin (EPO) in the carboxyl terminal region which are prepared by means of recombinant DNA techniques. These mutants have advantageous properties in comparison with human wild-type EPO.

4 Claims, 9 Drawing Sheets

MUTEINS OF HUMAN ERYTHROPOIETIN, THE PREPARATION THEREOF AND THE USE THEREOF

This application is a continuation of application Ser. No. 08/152,919, filed Nov. 16, 1993, now abandoned, which is a continuation application of Ser. No. 07/799,898, filed Dec. 2, 1991, now abandoned, which is a divisional application of Ser. No. 07/553,593, filed Jul. 18, 1990, now abandoned.

The application relates to muteins of human erythropoietin (EPO) which are prepared by means of recombinant DNA techniques and have advantageous properties in comparison with human wild-type erythropoietin.

Mature human erythropoietin is a glycoprotein having a molecular weight of 34 to 38 kD. The mature protein is composed of 166 amino acids (AA) and the glycosyl residue proportion of the molecular weight is about 40% (Jacobs et al., (1985), Nature 313, 806–809; Dordal et al., (1985), Endocrinology 116, 2293–2299).

The biological function of EPO is to guarantee the supply of erythrocytes. In doing so, EPO stimulates differentiation processes and also division processes in erythroid precursor cells.

The gene for human erythropoietin has been isolated from a fetal liver gene bank and characterized, and has been available for investigations in genetic engineering since 1985 (Jacobs et al., loc.cit.). Erythropoietin can be expressed in animal cells with the aid of recombinant DNA techniques, and it makes possible, inter alia, the treatment of renal anemia. Initial therapeutic experience with wild-type EPO showed that the rate of success was certainly very high in treated patients, but also showed that in some cases blood pressures and blood viscosities of a limiting value were reached. Thus the increase in hematocrit, hemoglobin and the number of precursor cells (burst-forming unit erythroid cells, BFU-E) was very drastic in some patients, it being desirable to have a moderate increase. With other patients the increase was too low, it being desirable to achieve a more pronounced increase in the blood counts. An unphysiological dose increase in poorly responding patients is contraindicated because of immune reactions which may be provoked. Long-term treatment is thereby made more difficult or even impossible.

It is very probable that the differing reactions of the patients derive from the individual abilities in each case to regulate the EPO doses. Therefore there are individual differing courses of therapy for EPO in different patients.

In addition to the structure of the protein moiety, the structure of the sugar side chains of the molecule are of particular importance in the interaction of the hormone with the body. For example, desialylated EPO shows no effect in animals after administration. Despite this it still binds to the receptor and stimulates precursor cells. The loss in activity in vivo of asialo-EPO can be explained by removal thereof in the liver by receptors with a specificity for galactosyl residues which are accessible in desialylated EPO. Even completely deglycosylated EPO still shows binding activity to the target cells in vitro but is excreted in the kidney faster in vivo via a mechanism which is still unknown. The EPO binding site for the receptor is therefore not altered by deglycosylation. However, the reduced action in vivo indicates that complete glycosylation and sialylation are important in transport in the blood, for stability and for the rate of elimination from the system.

In some patients the wild-type EPO which has been used therapeutically up to now causes an increase in blood pressure, which is a disadvantage in the treatment. Presumably EPO is involved in the regulation of blood pressure. It is therefore desirable to possess proteins with the physiological action of EPO which do not have these negative properties but still stimulate the differentiation and the rate of division of precursor cells to erythrocytes.

Stimulating megakaryocytes to form thrombocytes is a further side effect of EPO which occurs in some patients. In this case a risk of thrombosis can arise during the treatment with EPO, and the treatment must be stopped immediately. Here a higher specificity of the erythropoietin used is desirable.

The object on which the invention is based is to provide muteins of EPO. These muteins should possess an increased or reduced biological activity (=stimulation of erythrocyte formation) in order to make possible an individual treatment of the patients. Undesired side effects such as, for example, increased blood pressure should not be present or only to a limited extent.

We have found that the carboxyl terminal region (AA 130 to AA 166) contains a binding site to the EPO receptor. Deletions in this region lead to reduction or even to a loss of the biological activity, insertions of positively charged amino acids lead to an increase in the biological activity (=stimulation of the formation of erythrocytes from precursor cells). We have further found that there is a homology to angiotensin II in the region of amino acids 130 to 160 (more precisely: in the region of amino acids 142 to 149). Alterations in this region influence the vasopressor activity of EPO.

Additionally it has been found that reduced glycosylation leads to delayed stimulation of the erythrocyte formation.

The invention therefore relates to the following muteins of human EPO (1) Muteins of human erythropoietin which, in comparison with wild-type erythropoietin, show at least one amino acid deletion and/or one AA insertion or AA exchange in the region of amino acids 10–55, 70–85 and 130–166 and/or substitution of at least one of the N-glycosylated Asn by an amino acid which cannot be glycosylated and/or substitution of Ser 126 by Thr or Gly, so that they possess one or more altered properties in comparison with wild-type EPO in relation to (a) stimulating erythroid precursor cells, (b) in vivo half life, (c) increased blood pressure, (d) stimulating megakaryocytes and other precursor cells from the non-erythroid series, (e) side effects, for example occurrence of headaches, and (f) binding to the EPO receptor.

(2) In particular muteins which have an insertion in the region of the carboxyl terminal AA 130 to 166 are included. Furthermore, muteins with $Gly_{166}$ replacing $Arg_{166}$ or muteins containing on the carboxyl terminal one or more additional amino acids, preferably basic amino acids, attached to position 166 are preferred.

(3) Furthermore, muteins with at least one amino acid exchange in the region of amino acids 130 to 166 are particularly preferred.

(4) Furthermore, muteins under (1) with the serine in position 126 exchanged for threonine or glycine, or with at least one asparagine position which can be glycosylated exchanged for glutamin, with the exception of Asn 38, are preferred.

The present invention also relates to EPO muteins which show several or all of the abovementioned mutations at the same time, as has already been explained.

Finally the invention relates to medicaments which contain at least one of the above-described muteins and also to the use thereof in therapies which are aimed at an increase or reduction of the number and quality of erythrocytes, in particular in the treatment of renal anemia.

Finally the invention is included in the examples and the patent claims.

EXAMPLES

I. Preparation of EPO mutants (general methods)

1) Synthesis of EPO specific oligonucleotides.

Mutagenic oligonucleotides and primers for sequencing were prepared by the phosphate triester method (Letsinger, (1975), J. Amer. Chem. Soc. 97, 3278 and ditto (1976) J. Amer. Chem. Soc. 98, 3655). Examples of mutagenic oligonucleotides used are shown in Table 2.

2) Cloning of EPO c-DNA into the mutagenic vector system.

The EcoRI-BamHI fragment of 1024 bp, which contains the EPO encoding sequence and 3' thereof a SV40 DNA fragment containing the polyadenylation signal of the SV40 major late antigen (FIG. 1), was isolated from the vector pEPO 782 MT BPV (pCES, EP-A-267,678). The isolation of the fragment was achieved by cleaving the plasmid with the restriction endonuclease EcoRI and filling the recessed ends with the aid of the Klenow fragment of DNA polymerase I so that a blunt end results. The plasmid thus treated was then cut with the restriction enzyme BamHI and it was then possible to isolate the DNA fragment described above by elution from an agarose gel (Maniatis et al. (1982) Molecular Cloning—A Laboratory Manual, Cold Spring Harbor, N.Y.).

The fragment was then cloned directionally into the polylinker of the mutagenic vector pMac 5-8 (FIG. 1), which polylinker had been cut with SmaI-BamHI. This EPO wild-type construction was called pMcE1.

3) Mutagenesis

Synthetic oligonucleotides which contained the mutation (Table 2) were introduced into the mutagenic vector system via a so-called "gapped duplex" DNA hybrid molecule (Morinaga et al., Bio Technology, (1984), 7, 636–639; Kramer et al., Nucl. Acids. Res. 198, 12, 9441–9456) in the preparation of the mutants (Table 1). For this purpose single-stranded DNA of the mutagenic vector pMcE1 which had been introduced by transformation into E.coli strain WK6 was isolated by standard methods. Plasmid DNA from pMa 5-8 was cut in the polylinker with EcoRI-BamHI and the linearized DNA (3.8 kb) was eluted out of an agarose gel (Maniatis et al., loc.cit.).

For the preparation of a "gapped duplex" DNA, 0.1 pmol of double-stranded fragment (from pMA 5-8) (FIG. 1) and 0.5 pmol of single-stranded DNA (pMcE1) (FIG. 1) were heated at 100° C. for 4 minutes in 12.5 mMtris-HCl, pH 7.5+190 mM KCl (final volume 40 µl) and subsequently incubated at 65° C. for 10 minutes. Mutagenic oligonucleotide was incipiently hybridized by heating 8 µl of the hybridization solution mentioned to 65° C. for 5 minutes with 4–8 pmol (2 µl) of the enzymatically phosphorylated oligonucleotide, and was subsequently cooled slowly to room temperature. The addition of 24 µl H$_2$O, 4 µl 10× fill-in buffer (625 mM KCl, 275 mM tris-HCl pH 7.5, 150 mMMg Cl$_2$, 20 mM DTT, 0.5 mM ATP and 0.25 mM for each of the four NTPs), 1 µl T4 DNA ligase (5 U/µl) and 1 µl of Klenow fragment of DNA polymerase I (1 U/µl) was followed by incubation at room temperature for 45 minutes. 5 µl of the mixture were subsequently introduced by transformation into WK6 muts (mutS215: Tn10). The entire transformation mixture was multiplied overnight at 37° C. in an agitated culture in LB medium+50 µg/ml ampicillin (10 ml). The plasmid DNA was purified by standard methods from the entire mixture (Maniatis et al., loc.cit.).

Figure 1A:
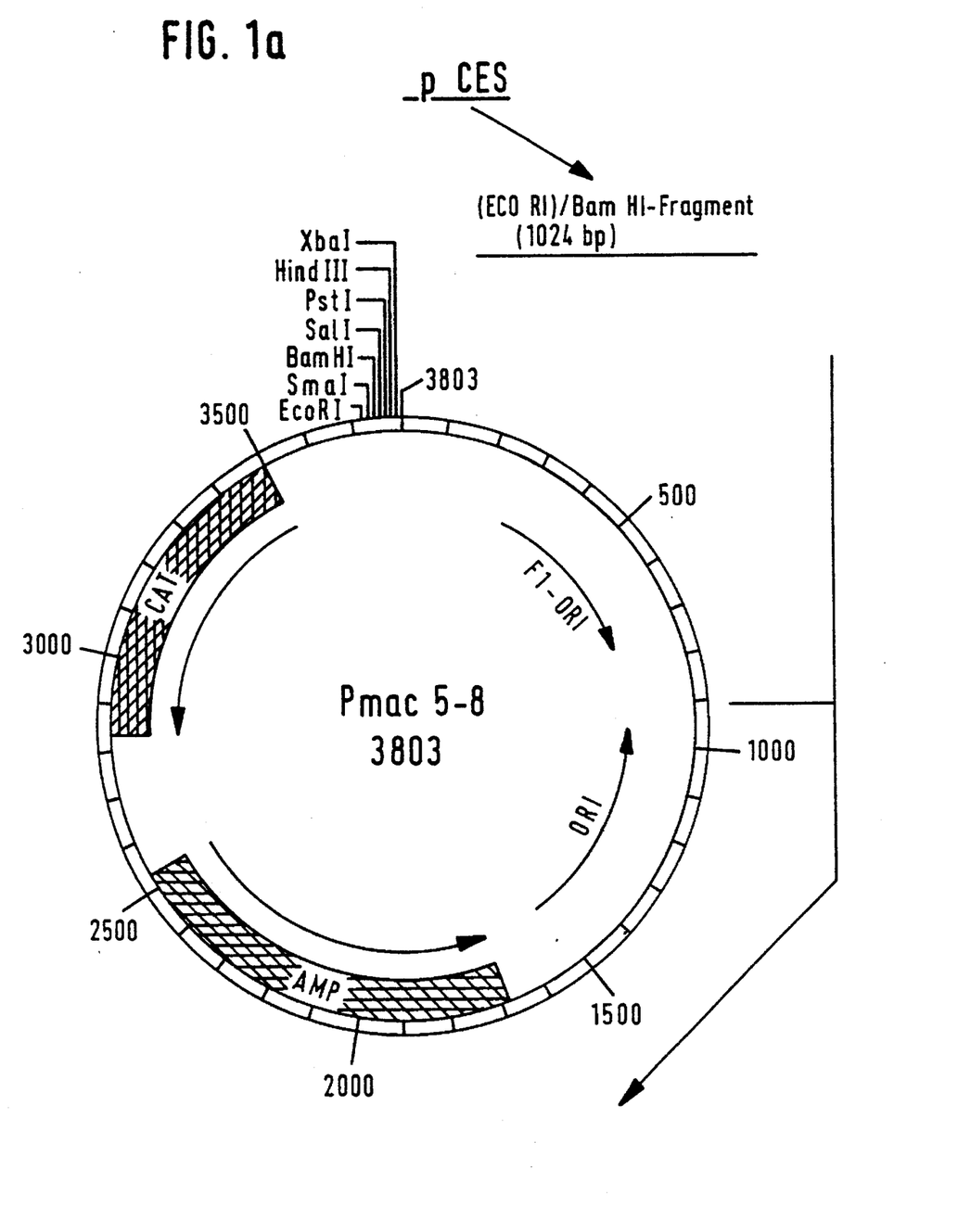
Figure 1B:
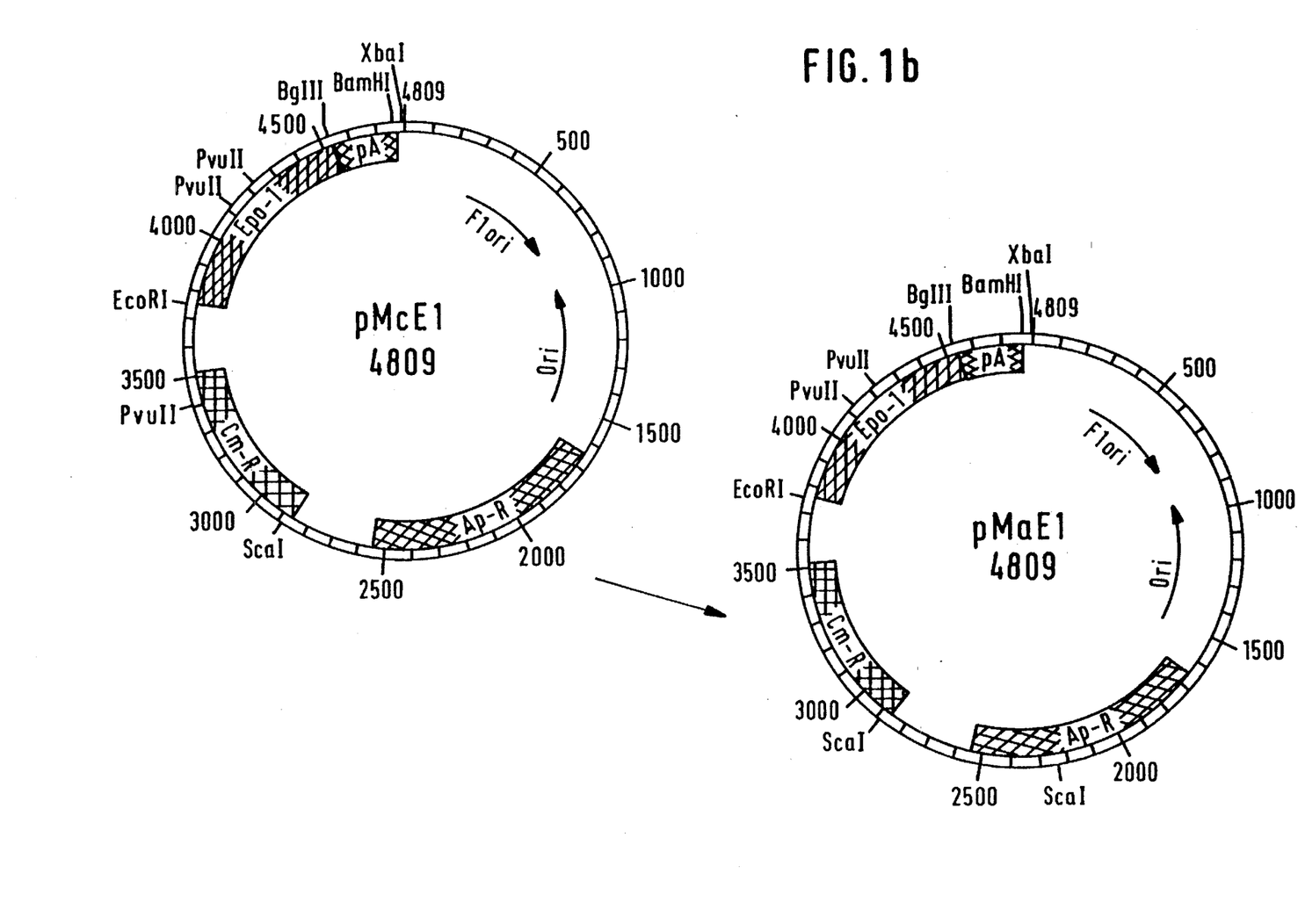

About 20 ng of the purified plasmid were introduced by transformation into WK6 bacteria and selection was carried out subsequently on LB plates containing 50 µg/ml ampicillin. Several of these mutants were initially analyzed roughly for the desired mutation by a suitable sequence reaction (C-, T-, A- or G-specific). Positive klones were confirmed by detailed sequence analysis in the region of the mutagenesis (F. Sanger et al., (1977), Proc. Natl. Acad. Sci, USA 74, 5463–5467). Plasmids containing mutated EPO sequences were termed as pMaE2, pMaE3 . . . pMaEn (FIG. 1).

4) Construction of an expression vector for EPO and EPO mutants

The expression vector pABL1 (FIG. 2) was prepared by removing the fragment coding for antithrombin III and the fragment containing the early polyadenylation site of SV40 from the expression vector pAB 3-1 (Zettlmeiβl et al., (1988), Behring Inst. Mitt. 82, 26–34) by cutting with the restriction enzymes HindIII and BamHI, and replacing the fragment by a polylinker of the following sequence:

5'ggatcccggggtaccgagctcgaattcatcgatatctagatctcgagctcgcgaaagctt3'

| BamHI | EcoRI | SacI | HindIII |

It was then possible—likewise via EcoRI and BamHI cleavage sites of the polylinker—to clone into the expression vector pABL1 fragments which had been cut out of the mutagenic vector system using EcoRI-BamHI before (E1, EPO wild-type) or after mutagenesis (E2-En, EPO mutants). The resulting EPO expression plasmids were named pABE1, pABE2, . . . pABEn (FIG. 2).

5) Transfection of animal cells and double selection

Figure 2A:
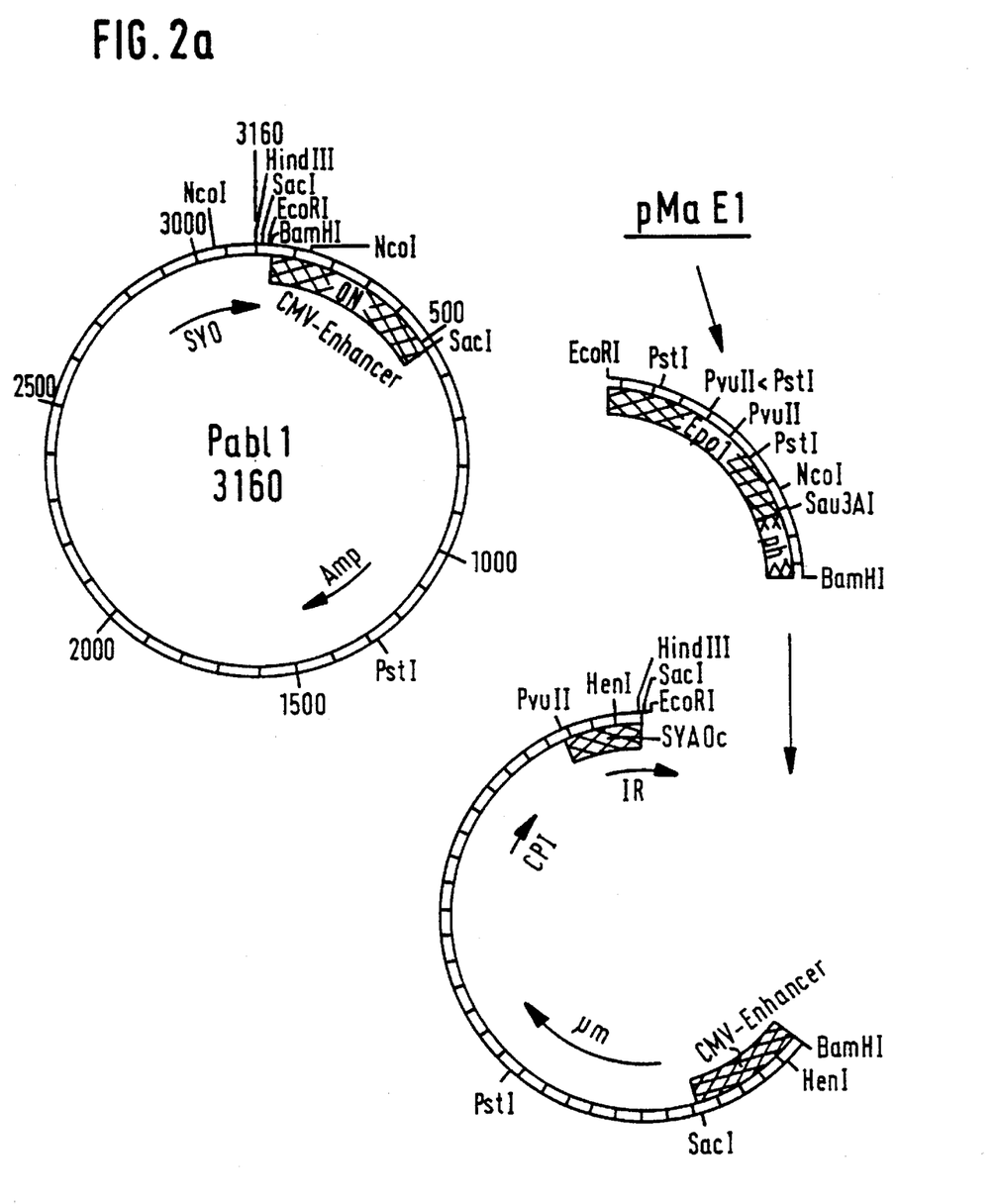
Figure 2B:
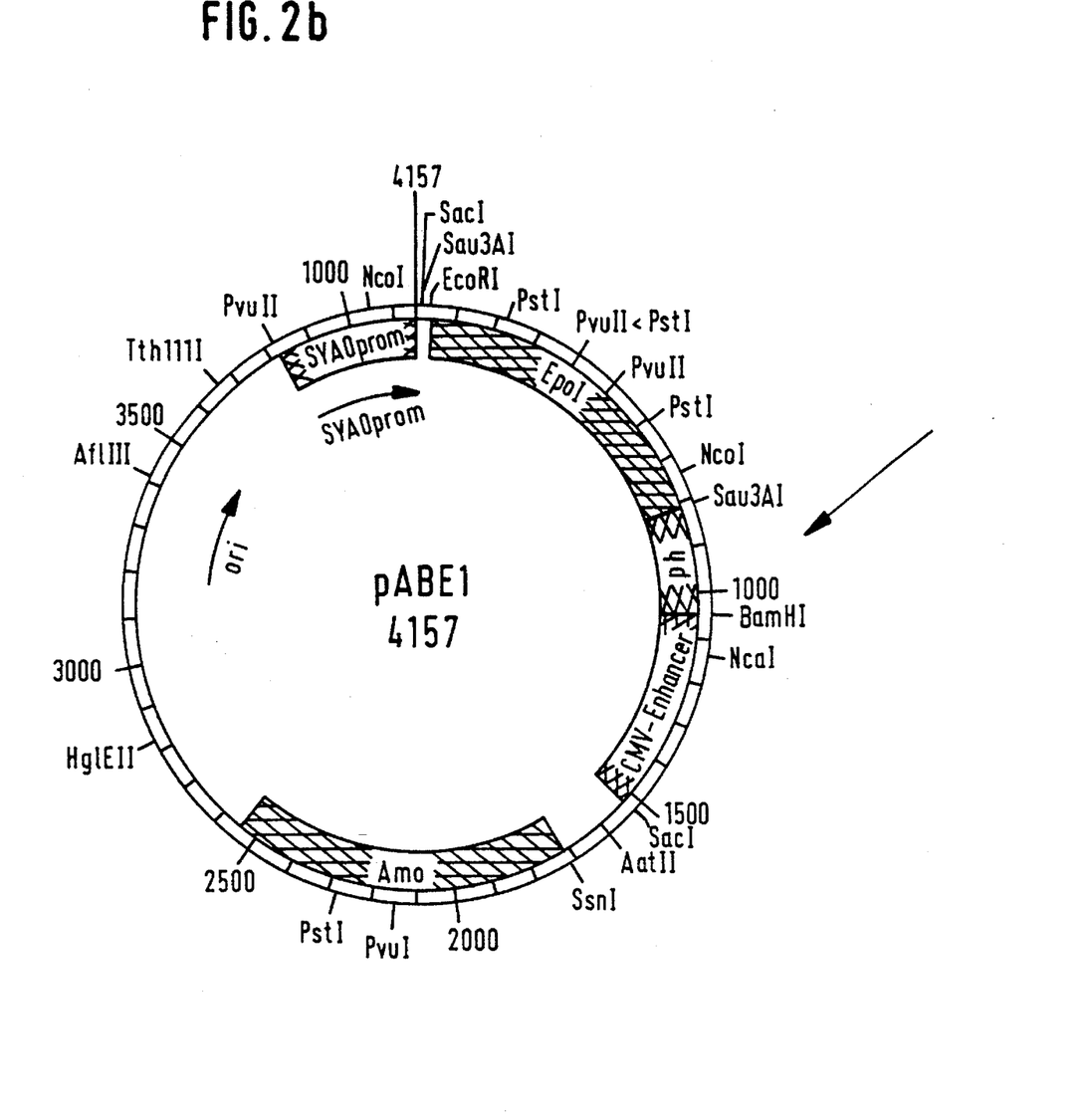

BHK21 cells (baby hamster kidney) (ATCCCCL10) were transfected with the EPO-coding expression vectors pABE1, pABE2, . . . pABEn (FIG. 2). For transfection, the cells were grown in Dulbecco's modified Eagle's medium (DMEM) which contained 10% of fetal calf serum. The cells were transfected at 50–70% confluence by means of a modified calcium phosphate method (Graham and van der Eb, (1973), Virology 52, 456–467).

The expression vector was cotransfected with the plasmid pSV2 dhfr (Lee et al., (1981), Nature (London) 294, 228–232) which contained a mouse dihydrofolate reductase (dhfr) gene which can be expressed in animal cells, and with plasmid pRMH140 (Hudziak et al., (1982), Cell 31, 137–146) which contained a geneticin resistance which can be expressed in animal cells. This system allows a double selection with methotrexat (1 mM) and geneticin (G418, 400 µg/ml) and allows an amplification of the plasmid DNAs which are integrated in the cellular genome (Zettlmeiβl et al., loc. cit.).

6) Immunological detection of EPO and EPO muteins from culture supernatants of expressing cells Preparation of antisera against EPO Antibodies against purified EPO were raised in rabbits. For this purpose EPO was coupled to keyhole limpet hemocyanine (KLH) with the aid of glutaric dialdehyde, and an emulsion with adjuvants was prepared and used for immunization. The sera were obtained by standard methods.

Radioimmunoassay for measuring erythropoietin

This test is used for the quantitative determination of recombinant EPO in cell culture supernatants and in samples from different stages of purification of the hormone. It is based on the two-antibodies variant of the competitive radioimmunoassay (C. N. Hales, P. J. Randle, (1983), Biochem., J. 88, 137).

Samples or calibration material was incubated together with a predetermined amount of $^{125}I$ EPO and anti-EPO rabbit antiserum at 4° C. for 24 hours and was then incubated with goat anti-rabbit IgG at 4° C. for a further 18 hours to separate off the $^{125}I$ EPO bound by antibodies. The precipitate was separated off by centrifugation, washed twice with 500 μl of buffer in each case and measured in the gamma channel of an automatic gamma spectrometer. The system contained pooled rabbit normal serum in order to enhance precipitation. Evaluation was carried out by comparison with a series of dilutions of the calibration material by means of calibration plots in which the binding of radioactivity in percent was plotted against the decimal logarithm of the calibration material concentration.

The $^{125}I$ EPO was obtained from purified EPO by iodine radiolabeling using the two-phase chloramine-T method (F. Tejedor, J. P. G. Ballesta, (1982), Anal. Biochem. 127, 143–149), and unincorporated iodide was removed by gel chromatography. The anti-EPO serum was prediluted in a 1:3300 ratio, and the anti-rabbit IgG serum was diluted 150-fold. A laboratory standard prepared from pure recombinant human EPO, the protein content of which had been determined using the BCA method (P. K. Smith, (1985), Anal. Biochem. 150, 76–85), was used as the calibration material. Using an antiserum against the entire EPO molecule also guaranteed the detection of the EPO muteins.

Enzyme immunoassay for identifying EPO-producing cell clones.

An ELISA/dot blot test system was developed for rapid screening (no dilution necessary) of EPO-producing cell lines. 200 μl of culture supernatant are aspirated onto nitrocellulose. The filters were saturated with 0.5% BSA in PBS pH 7.0 at 37° C. for 30 minutes, and were subsequently incubated overnight with anti-EPO rabbit antiserum diluted 1:1000. The filters were washed with PBS 0.05% Tween and subsequently incubated for 2 hours with a goat anti-rabbit Ig antiserum which is coupled with alkaline phosphatase. After further washing with 0.05% Tween in PBS pH 7.0 and 0.2M tris-HCl pH 9.5 and also 1 M tris-HCl pH 9.5, p-nitro blue tetrazolium chloride hydrate and the p-toluidine salt of 5-bromo-4-chloroindolyl phosphate were added as substrates. The reaction is stopped after 20 minutes by the addition of water. The test is suitable for the detection of amounts of EPO larger than 100 ng EPO/ml. Purified recombinant EPO from C127 cells (EP-A-267,678) was used as the calibration material.

7) Detection of the biological activity of EPO and EPO muteins from culture supernatants of transfected and stable expressing cells.

in vivo Bioassay

NMRI mice from the animal breeding of Behringwerke AG (Marburg, FRG) were randomly separated into groups and were intraperitoneally injected with different doses of EPO or EPO muteins twice per day on five consecutive days. Control animals were treated with PBS, cell culture medium or cell culture supernatant of BHKcells. Purified recombinant EPO from C127 cells (EP-A-267,678) was used as the calibration material. Hematological examinations were carried out at several times between day 0 and day 22 after injection of the first EPO dose, the examinations comprising the determination of the hematocrit, the hemoglobin content and the number of reticulocytes in the peripheral blood.

in vitro Bioassay

Female NMRI mice were injected with phenylhydrazine hypochloride (60 mg/ml) on two consecutive days. 48 hours after the last injection the spleens were dissected and a single-cell suspension was prepared. From these cells the erythroid precursor cells were enriched via a Ficoll gradient (D=1.077). The interphase of the gradient was collected, washed twice with 20 ml of PBS, resuspended in DMEM and the cells were counted. EPO and EPO mutein samples were diluted and 20 μl of each dilution were added in each case to 80 μl of spleen cell suspension in a microtiter plate ($3\times10^5$ cells/well). After 22 hours of incubation in a humid atmosphere and 5% $CO_2$, 1 μCi of methyl-$^3H$-thymidine in 20 μl of DMEM were added to each well. The cells were labeled for 3 hours and the $^3H$ incorporation was then measured in a TRI-CARB 6660 liquid scintillation counter (Krystal et al., J. Exp. Hematol. 11, 649). The calibration materials were PBS, medium and purified recombinant EPO from C127 cells (EP-A-267,678).

8) Isolation of EPO- and EPO-mutein-producing cell clones from mixed clones of transfected BHK cells Mixed BHK clones which originated in a pool of 80–100 single clones after transfection and double selection were tested for secretion of EPO or EPO muteins using immunoassays and bioassays. Positive mixed clones produced 100 ng–1 μg of EPO or EPO mutein. It was possible to obtain single-cell clones which produced between 1 to 10 μg of EPO or EPO mutein, after cloning by a limiting dilution process. A comparable EPO production in mixed clones which produced less EPO or EPO mutein could be achieved by amplification selection with methotrexat. The biological activity in vitro (standardization by RIA or ELISA) from these unpurified preparations is comparable with the activity in purified EPO fractions (100 U/μg–200 U/μg). The muteins show a different biological activity in vivo in comparison with rhuEPO-WT (FIGS. 3 and 4). In order to prepare larger amounts of cell culture supernatants, the single clones were expanded until it was possible to cultivate them in roller bottles. The growth of the cells was carried out in serum-containing medium (DMEM) up to confluence. Cultures were then switched to serum-free medium (DMEM). The culture supernatants were harvested after three days of cultivation in serum-free medium. It was possible to achieve a comparable EPO production in mixed cell clones which produced less EPO or EPO mutein by amplification selection with methotrexat.

II. Specific muteins (names see Table 1)

1. Mutein EPO 3

The carboxyl terminal arginine 166 was exchanged for glycine with the aim of obtaining erythropoietin mutein which is only slightly altered and should therefore have very similar biological properties to the wild-type EPO. It was possible to show in a detailed structural analysis that arginine 166 is, in any case, missing both in recombinant EPO and in wild-type EPO which was isolated from urine, so that the physiologically active EPO is probably a des-Arg-166 EPO (M. A. Recny et al., (1987), J. Biol. Chem. 262, (35) 17156–63). The mutein EPO 3 exhibits the same migratory behavior in an SDS-polyacrylamide gel (SDS-PA gel) as wild-type EPO (34–38 kD) and, in the in vivo bioassay, exhibits functional properties which cannot be distinguished from those of the wild-type molecule (FIGS. 3 and 4). All mixed clones produce mutein and a single clone could be isolated which produced 7.5 μg/ml/$10^6$ cells/24 hours. The expression rates of the various cell clones were substantially higher in comparison with wild-type EPO-producing cell clones.

2. Mutein EPO 7

The N-glycosylation site at Asn24 was removed by an exchange with Gln24. The mutant exhibits the same migratory behavior in an SDS-PA gel between 34 and 38 kD as wild-type EPO. There is a delayed stimulation of reticulocyte growth in the biological in vivo test (FIGS. 3 and 4). All mixed EPO 7 clones produced mutein and single clones could be isolated which produced up to 3.1 μg/ml/$10^6$ cells/24 hours.

3. Mutein EPO 10

EPO also contains an O-glycosylation site at the amino acid Ser126. When Ser126 is substituted by Thr126, several bands form in an SDS-PA gel, all of which have a lower molecular weight (30 kD to 25 kD) than authentic EPO. This may be caused by a heterogeneous glycosylation pattern. Although the threonine can also be O-glycosylated, it seems, however, to be O-glycosylated in a different form to the serine in authentic erythropoietin in this example. The in vivo stimulation of reticulocyte growth and the increase of hematocrit and hemoglobin content is delayed as in the abovementioned examples (FIGS. 3 and 4). However, in a study of the kinetics it seems as though the reticulocyte reservoir would be depleted more rapidly than by EPO or the other muteins. All mixed transfectant clones produced mutein EPO 10 and single clones could be isolated which secreted up to 2.8 μg/ml/$10^6$ cells/24 hours into the medium.

4. Muteins EPO 44a, 44b and 45

EPO has a homology to angiotensin II in the region of amino acids 142 to 149. Angiotensin is formed via the renin-angiotensin system in the body and effects a vasoconstriction which leads to an increase in blood pressure. Muteins which do not cause high blood pressure and can therefore also be used in patients with hypertension are prepared by exchanging amino acids in this region. Additionally, side effects, such as headaches, caused by increased blood pressure do not occur.

5. Muteins 2b, 2c, 2d1, 2d2, 2e, 2f, 4a, 4b, 5a, 5b, 6a, 6b

Additions of basic amino acids in the carboxyl terminal region increase biological activity of EPO (increased reticulocyte formation in vivo; increased depletion of the reticulocyte reservoir). Deletions lead to reduced activity of EPO.

TABLE 1

| #  | EPO  | Variant | Description |
|----|------|---------|-------------|
| 1  | EPO  | 1       | (wild-type) Arg 166 |
| 2  | EPO  | 2a      | C-terminal deletion 1 amino acid Asp 165 |
| 3  | EPO  | 2b      | C-terminal deletion 2 amino acid, Gly 164 |
| 4  | EPO  | 2c      | C-terminal deletion 3 amino acid, Thr 163 |
| 5  | EPO  | 2d1     | C-terminal deletion 4 amino acid, Arg 162 |
| 6  | EPO  | 2d2     | C-terminal deletion 4 amino acid, Arg 162 + Ala 163 |
| 7  | EPO  | 2e      | C-terminal deletion 5 amino acid, Cys 161 |
| 8  | EPO  | 2f      | C-terminal deletion 6 amino acid, Ala 160 |
| 9  | EPO  | 3       | C-terminal exchange Arg 166 – Gly 166 |
| 10 | EPO  | 4a      | C-terminal insertion Arg 166 + Arg 167 |
| 11 | EPO  | 4b      | C-terminal insertion Arg 166 + Arg 167 + Ala 168 |
| 12 | EPO  | 5a      | C-terminal insertion Arg 166 + Arg + Lys + Arg 169 |
| 13 | EPO  | 5b      | C-terminal insertion Arg 166 + Arg + Lys + Arg + Ala 170 |
| 14 | EPO  | 6a      | C-terminal insertion Arg 166 + poly Lys 167 – 176 |
| 15 | EPO  | 6b      | C-terminal insertion Arg 166 + poly Lys 167 – 176 + Ala 177 |
| 16 | EPO  | 7       | glycosylation Asn 24 – Gln 24 |
| 17 | EPO  | 9       | glycosylation Asn 83 – Gln 83 |
| 18 | EPO  | 10a     | glycosylation Ser 126 – Thr 126 |
| 19 | EPO  | 10b     | glycosylation Ser 126 – Gly 126 |
| 20 | EPO  | 42a     | exchange Tyr 15 – Phe 15 |
| 21 | EPO  | 42b     | exchange Tyr 15 – Ala 15 |
| 22 | EPO  | 43a     | exchange Tyr 49 – Phe 49 |
| 23 | EPO  | 43b     | exchange Tyr 49 – Ala 49 |
| 24 | EPO  | 44a     | exchange Tyr 145 – Phe 145 |
| 25 | EPO  | 44b     | exchange Tyr 145 – Ala 145 |
| 26 | EPO  | 45      | exchange Arg 143 – Ala 143 |
| 27 | EPO  | 46a     | exchange Tyr 156 – Phe 156 |
| 28 | EPO  | 46b     | exchange Tyr 156 – Ala 156 |
| 29 | EPO  | 47      | exchange Arg 76/Gln 78 – Ala 76/Ala 78 |
| 30 | EPO  | 48      | exchange Arg 76 – Ala 76 |
| 31 | EPO  | 49      | exchange Gln 78 – Ala 78 |

TABLE 2a

| | |
|---|---|
| EPO 3    | 5'cacctggtcacccgtgccctgtcctgcaggcc 3' |
| EPO 4    | 5'cacctggtcatcttctgtgccctgtcctgcaggcc 3' |
| EPO 4a   | 5'cacctggtcaggctcttctgtgccctgtcctgcaggcc 3' |
| EPO 5    | 5'cacctggtcatcttttctgtgccctgtcctgcaggcc 3' |
| EPO 5a   | 5'cacctggtcaggctcttttctgtgccctgtcctgcaggcc 3' |
| EPO 6    | 5'cacctggtcacttcttcttcttcttcttcttctttctgtccctgtcctgcaggcc 3' |
| EPO 6a   | 5'cacctggtcaggccttcttcttccttcttcttcttcttcttctttctgtccctgtcctgcaggcc 3' |
| EPO wt   | 5'cacctggtcatctgtccctgtcctgcaggcc 3' |
| EPO 2a   | 5'cacctggtcagtccctgtcctgcaggcc 3' |
| EPO 2b   | 5'cacctggtcaccctgtcctgcaggcc 3' |
| EPO 2c   | 5'cacctggtcatgtcctgcaggcc 3' |
| EPO 2d1  | 5'cacctggtcacctgcaggcc 3' |
| EPO 2d2  | 5'cacctggtcagccctgcaggcc 3' |
| EPO 2e   | 5'cacctggtcagcaggcctcccc 3' |
| EPO 2f   | 5'cacctggtcaggcctcccc 3' |

TABLE 2b

| | |
|---|---|
| EPO 7    | 5'gcccgtcgtgatctgctcggcctcc 3' |
| EPO 9    | 5'cggctgggaagactggacccacagggcc 3' |
| EPO 10a  | 5'cggagtggagcagcagtggccgcatctggagggg 3' |
| EPO 10b  | 5'cggagtggagcagccccggccgcatctggagggg 3' |
| EPO 42a  | 5'cctccaagagaaacctctcc 3' |
| EPO 42b  | 5'cctccaagaggcccctctcc 3' |
| EPO 43a  | 5'ccaggcaaagaaattaac 3' |
| EPO 43b  | 5'ccaggcgccgaaattaac 3' |
| EPO 44a  | 5'ggaaattggaaaagactcgg 3' |
| EPO 44b  | 5'ggaaattggagccgactcgg 3' |
| EPO 45a  | 5'gcctccccctgtaaacagcttcagc 3' |
| EPO 45b  | 5'ggctcccctgtgcccagcttcagc 3' |
| EPO 46   | 5'ggagtagactgcgaagag 3' |
| EPO 47   | 5'cagggccgcccgcgccaggac 3' |
| EPO 48   | 5'ggcctggcccgccaggac 3' |

TABLE 2b-continued

| EPO 49 | 5'cagggccgcgccccgcagg 3' |

Figure 3A:
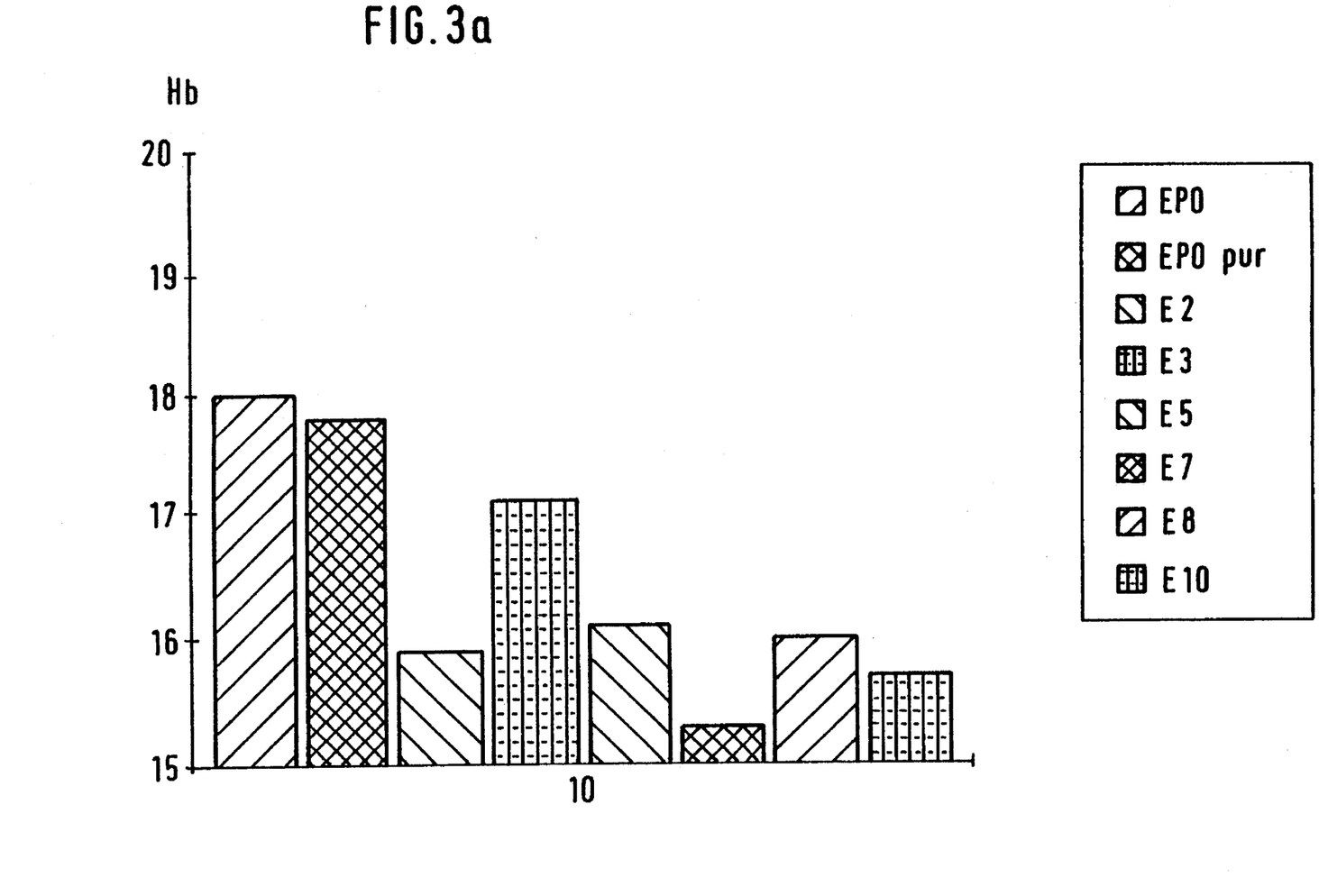
Figure 3B:
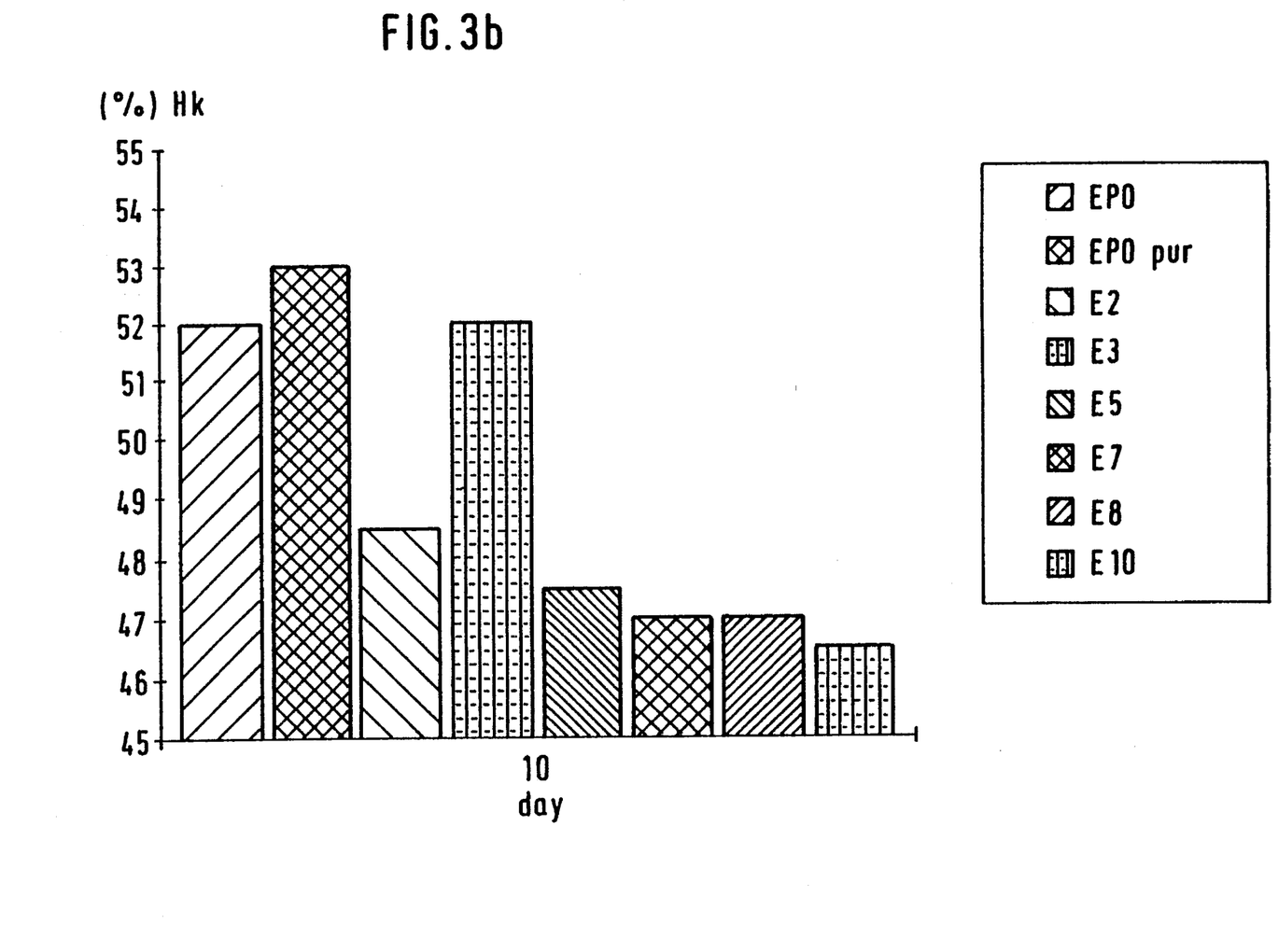
Figure 3C:
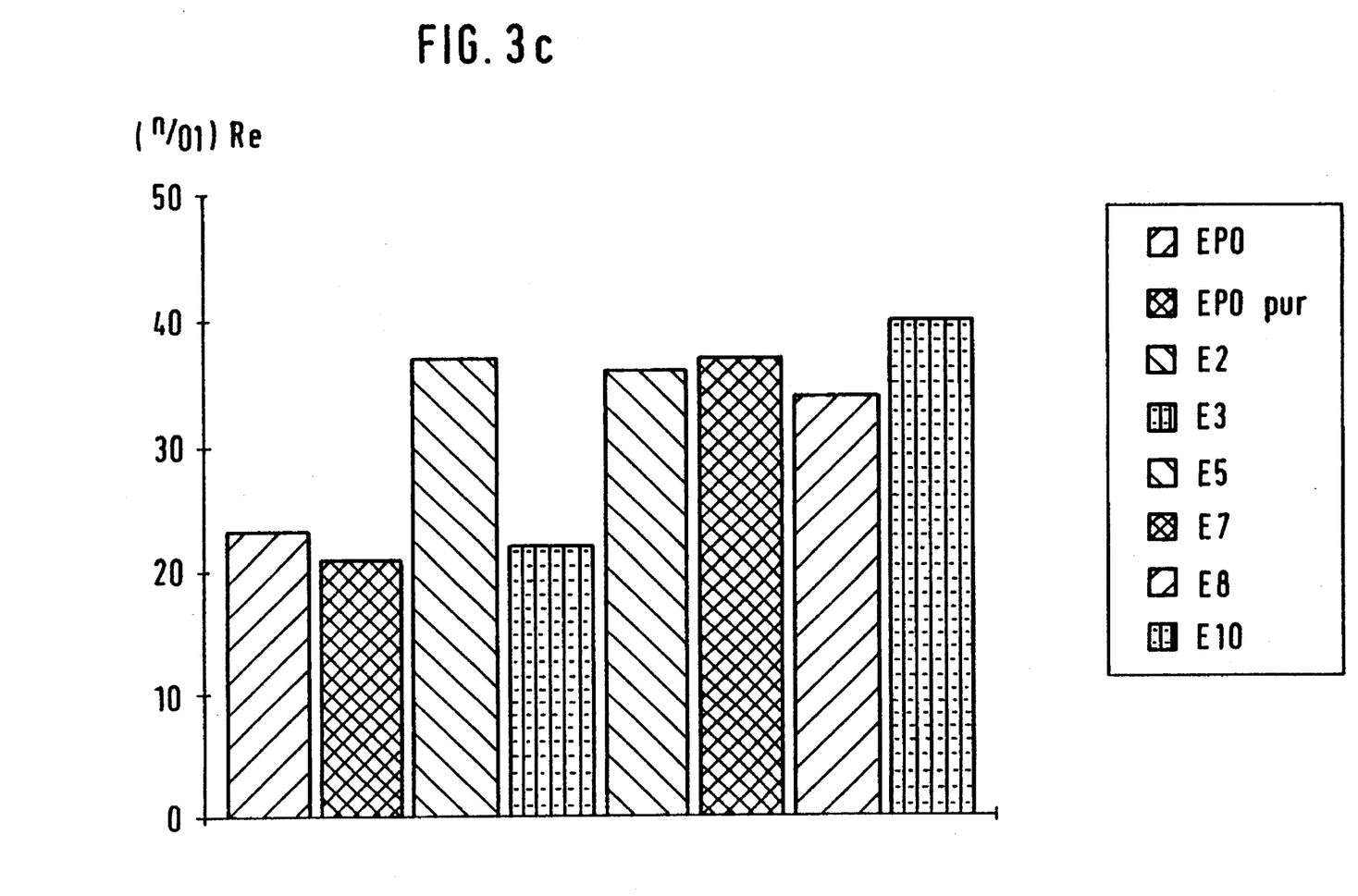
Figure 4A:
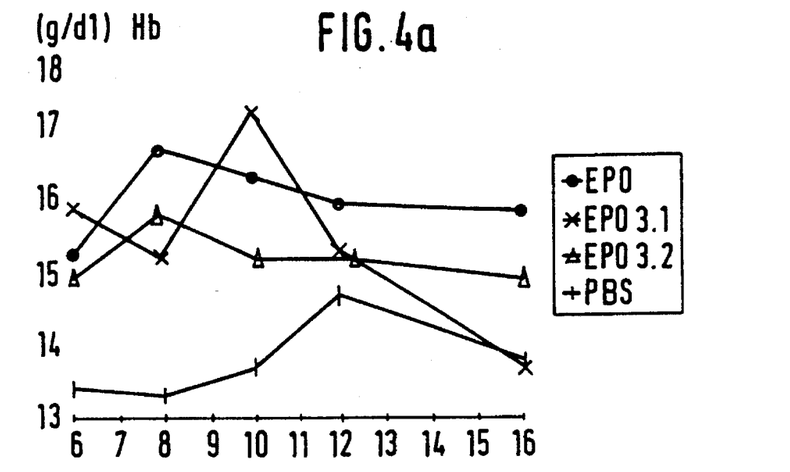
Figure 4B:
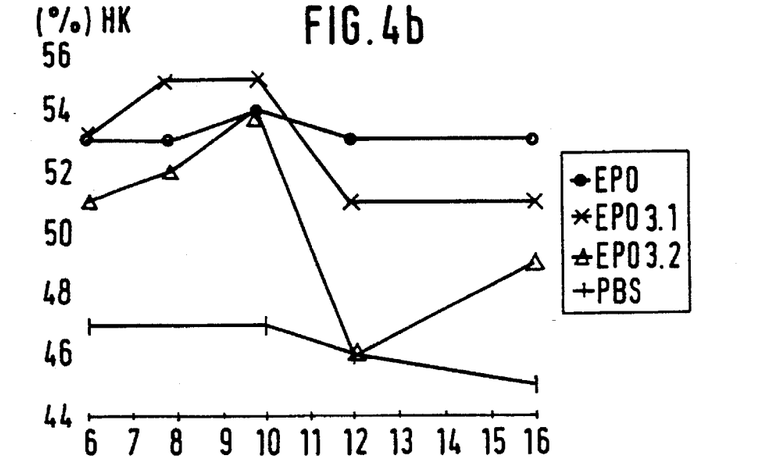
Figure 4C:
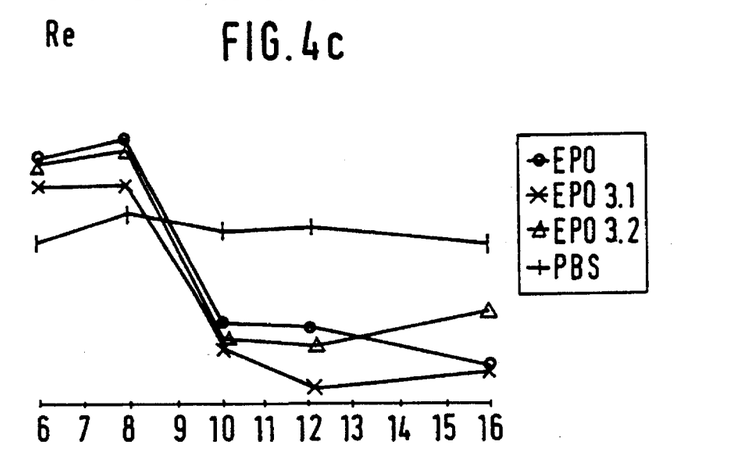
Figure 5A:
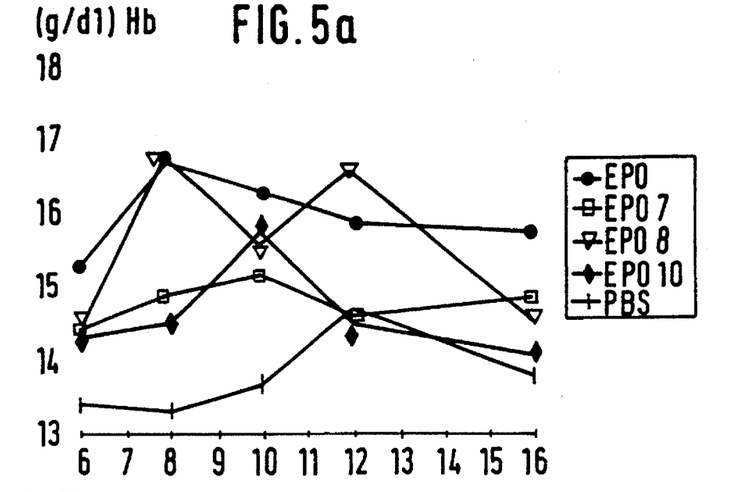
Figure 5B:
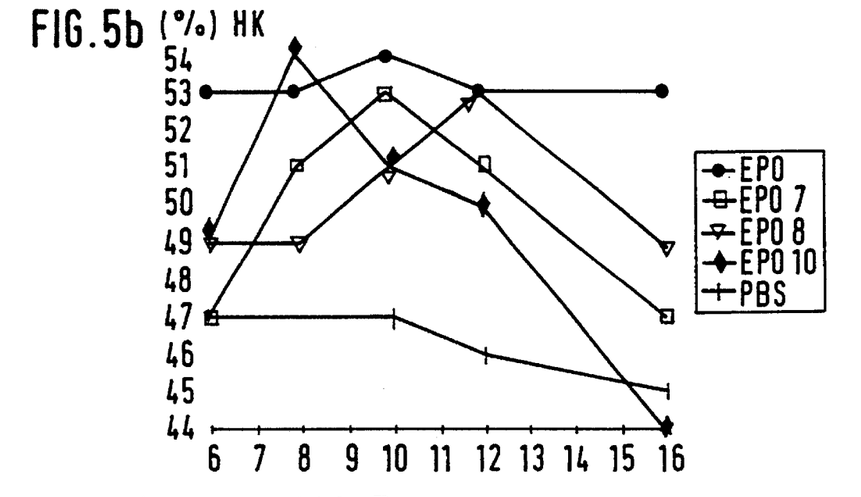
Figure 5C:
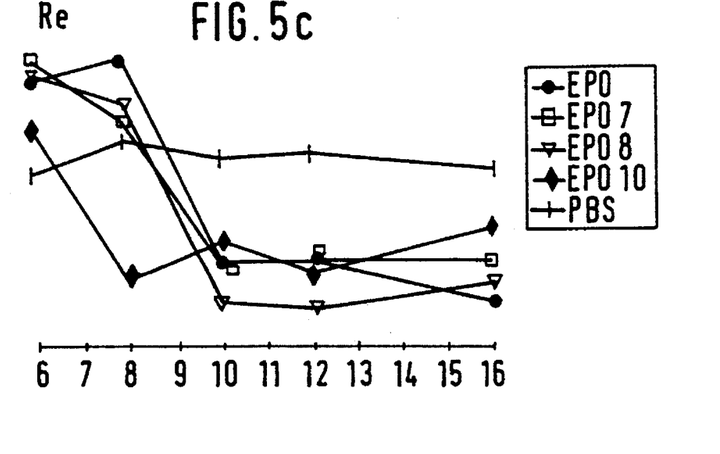

Legend of FIGS. 3a–c

The action of EPO muteins was tested in vivo. Hemoglobin and hematocrit values and the number of reticulocytes in NMRI mice which had been treated with the concentrated cell culture supernatants containing the EPO mutein were determined. Determinations were carried out on day 10 after the treatment. A purified wild-type EPO from C127i mice cells (EPO pur) was used as control.

Hb=hemoglobin, Hk=hematocrit, Re=reticulocyte number

Legend of FIGS. 4a–c and 5a–c

The pattern of the hemoglobin and hematocrit values and of the reticulocyte number of NMRI mice after treatment with EPO and EPO muteins. Purified EPO (EPO pur) or concentrated culture supernatants which contained equal amounts of EPO mutein were injected into untreated NMRI mice on day 0, and the hemoglobin and hematocrit values and the reticulocyte number were determined. The different determinations were carried out at different times from day 5 after treatment to day 16.

Hb=hemoglobin, Hk=hematocrit, Re=reticulocyte number

We claim:

1. A process comprising administration of a medicament to a host to increase the number or quality of erythrocytes of said host, wherein said medicament comprises an effective amount of human erythropoietin in which Asn 24 is substituted by Gln 24.

2. The process of claim 1, wherein said administration is for treatment of renal anemia.

3. A method of treatment of a host comprising administration of a medicament to a host in need of an increase in the number or quality of erythrocytes, wherein said medicament comprises an effective amount of human erythropoietin in which Asn 24 is substituted by Gln 24.

4. The method of treatment in claim 3, wherein said administration is for treatment of renal anemia.

* * * * *